(12) United States Patent
Martin et al.

(10) Patent No.: US 9,765,303 B2
(45) Date of Patent: Sep. 19, 2017

(54) METHOD FOR THE PRODUCTION OF DIFFERENTIATED RESPIRATORY EPITHELIAL CELLS

(75) Inventors: Ulrich Martin, Sehnde (DE); Christina Mauritz, Hannover (DE)

(73) Assignee: MEDIZINISCHE HOCHSCHULE HANNOVER, HANNOVER (DE)

( * ) Notice: Subject to any disclaimer, the term of this patent is extended or adjusted under 35 U.S.C. 154(b) by 142 days.

(21) Appl. No.: 13/983,299

(22) PCT Filed: Feb. 3, 2012

(86) PCT No.: PCT/EP2012/051818
§ 371 (c)(1),
(2), (4) Date: Sep. 30, 2013

(87) PCT Pub. No.: WO2012/104400
PCT Pub. Date: Aug. 9, 2012

(65) Prior Publication Data
US 2014/0017691 A1     Jan. 16, 2014

(30) Foreign Application Priority Data

Feb. 4, 2011   (EP) .................................... 11000905
Feb. 7, 2011   (EP) .................................... 11000958

(51) Int. Cl.
*C12N 5/071*      (2010.01)
*C12Q 1/68*       (2006.01)
*G01N 33/50*      (2006.01)

(52) U.S. Cl.
CPC ......... *C12N 5/0688* (2013.01); *C12Q 1/6881* (2013.01); *C12Q 1/6897* (2013.01); *G01N 33/5044* (2013.01)

(58) Field of Classification Search
None
See application file for complete search history.

(56) References Cited

FOREIGN PATENT DOCUMENTS

| EP | 2218778 | 8/2010 |
| WO | WO-2007/121443 | 10/2007 |
| WO | WO 2009/115295 | 9/2009 |
| WO | WO 2009/144008 | 12/2009 |

OTHER PUBLICATIONS

Borok, Zea, et al. "Keratinocyte growth factor modulates alveolar epithelial cell phenotype in vitro: expression of aquaporin 5." American Journal of Respiratory Cell and Molecular Biology 18.4 (1998): 554-561.*
Fujino, Naoya, et al. "Isolation of alveolar epithelial type II progenitor cells from adult human lungs." Laboratory Investigation 91.3 (2011): 363-378.*
Schmeckebier, Sabrina, et al. "Keratinocyte growth factor and dexamethasone plus elevated cAMP levels synergistically support pluripotent stem cell differentiation into alveolar epithelial type II cells." Tissue Engineering Part A 19.7-8 (2013): 938-951.*
Berg, et al. Glucocorticoids regulate the CCSP and CYP2B1 promoters via C/EBPbeta and delta in lung cells. Biochem Biophys Res Commun. 293:907-912 (2002).
Coraux et al. Embryonic stem cells generate airway epithelial tissue. Am J Respir Cell Mol Biol. 32:87-92 (2005).
Fehrenbach, et al. Keratinocyte growth factor-induced proliferation of rat airway epithelium is restricted to Clara cells in vivo. Eur Respir J. 20:1185-1197 (2002).
Gadue, et al. WNT and TGF-beta signaling are required for the induction of an in vitro model of primitive streak formation using embryonic stem cells. Proc Natl Acad Sci USA 103:16806-16811 (2006).
Gonzales, et al. Differentiation of human pulmonary type II cells in vitro by glucocorticoid plus cAMP. Am J Physiol Lung Cell Mol Physiol. 283:L940-951 (2002).
Guan et al. Pluripotency of spermatogonial stem cells from adult mouse testis. Nature 440: 1199-1203 (2006).
Matsui et al. Effect of *Steel* factor and leukaemia inhibitory factor on murine primordial germ cells in culture. Nature 353: 750-752 (1991).
Mouhieddine-Gueddiche et al. Dexamethasone potentiates keratinocyte growth factor-stimulated sp-a and sp-b gene expression in alveolar epithelial cells. Pediatric Research 53:231-239 (2003).
Resnick et al. Long-term proliferation of mouse primordial germ cells in culture. Nature 359: 550-551 (1992).
Revazova et al. Patient-specific stem cell lines derived from human parthenogenetic blastocysts. Cloning and Stem Cells 9:432-449 (2007).
Roszell et al. Efficient derivation of alveolar type II cells from embryonic stem cells for in vivo application. Tissue Engineering: Part A 15:3351-3365 (2009).
Sueblinvong et al. Derivation of lung epithelium from human cord blood-derived mesenchymal stem cells. Am J Respir Crit Care Med. 177:701-711 (2008).
Takahashi et al. Induction of Pluripotent Stem Cells from Mouse Embryonic and Adult Fibroblast Cultures by Defined Factors. Cell 126: 663-676 (2006).

(Continued)

*Primary Examiner* — Robert Yamasaki
(74) *Attorney, Agent, or Firm* — Wilson Sonsini Goodrich & Rosati

(57) ABSTRACT

The present invention relates to a method for the production of differentiated respiratory epithelial cells comprising: (a) providing a cell population comprising or consisting of precursor cells of respiratory epithelial cells; (b) culturing the cell population of (a) in culture medium to which keratinocyte growth factor has been added; wherein the cultured cell population is supplemented with a glucocorticoid, a cAMP analog and a cAMP elevating agent and wherein said supplementation is either simultaneously with the addition of keratinocyte growth factor in step (b) or prior or subsequently to the addition of keratinocyte growth factor in step (b), thereby differentiating said precursor cells into respiratory epithelial cells. The present invention further relates to the cell(s) obtained by the method of the invention for use in treating or preventing a respiratory disease and to a method for identifying a compound having an pharmacological, cytotoxic, proliferative, transforming or differentiating effect on the differentiated respiratory epithelial cells obtained by the method of the invention.

23 Claims, 4 Drawing Sheets

(56) References Cited

OTHER PUBLICATIONS

Figure 1:
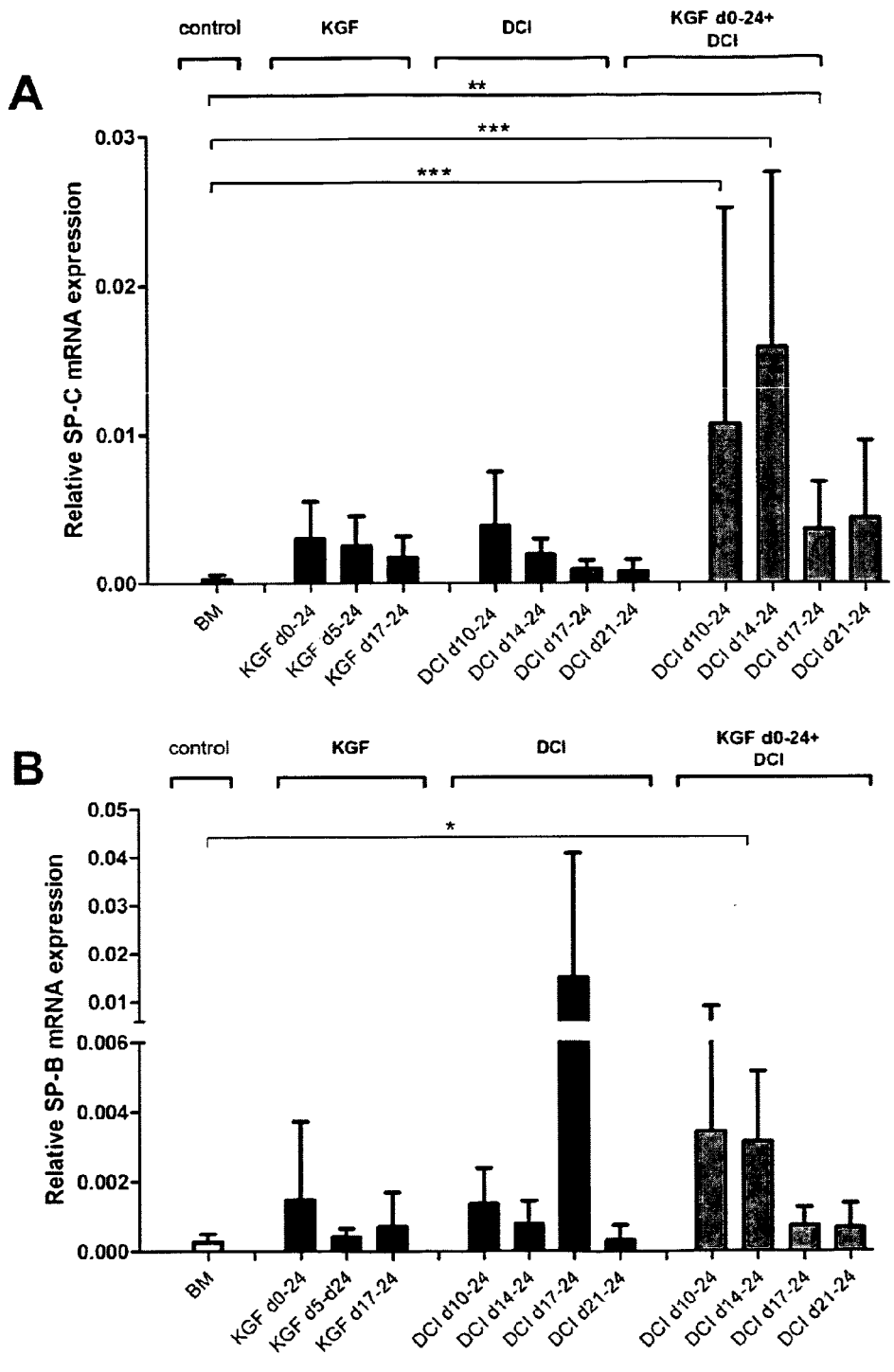
Figure 1:
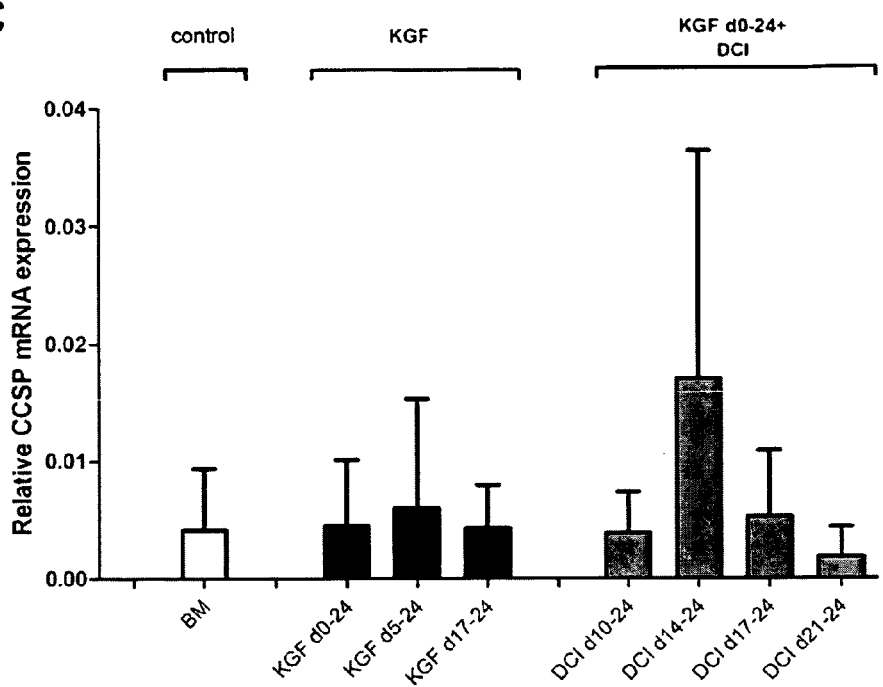

Wang et al. Transplantation of Human Embryonic Stem Cell—Derived Alveolar Epithelial Type II Cells Abrogates Acute Lung Injury in Mice. Molecular Therapy 1-10 (2010) (On-line version).
Wernig, et al. In vitro reprogramming of fibroblasts into a pluripotent ES-cell-like state. Nature 448:318-324 (2007).
Winkler, et al. Serum-Free Differentiation of Murine Embryonic Stem Cells into Alveolar Type II Epithelial Cells. Cloning Stem Cells 10:49-64AC (2008).
Yano, et al. KGF regulates pulmonary epithelial proliferation and surfactant protein gene expression in adult rat lung. Am J Physiol Lung Cell Mol Physiol. 279:L1146-1158 (2000).
Lin, et al., "Effects of fibroblast growth factors on the differentiation of the pulmonary progenitors from murine embryonic stem cells", Experimental Lung Research vol. 36, No. 5, Jun. 1, 2010 (Jun. 1, 2010), pp. 307-320.
PCT/EP2012/051818 International Search Report dated May 29, 2012.
Sugahara, et al. "Alveolar epithelial cells: differentiation and lung injury.", Respirology (Carlton, Vic.) Jan. 2006 LNKD—Pubmed:16423267, vol. 11 Suppl, Jan. 2006 (Jan. 2006), pp. S28-S31.
Wang, et al. "Differentiated human alveolar epithelial cells and reversibility of their phenotype in vitro." *Am J Respir Cell Mol Biol.* 2007;36:661-668.
Wang, et al. "Differentiated Human Alveolar Type II Cells Secrete Antiviral IL-29 (IFN-lambda 1) in Response to Influenza A Infection", Journal of Immunology, vol. 182, No. 3, Feb. 2009 (Feb. 2009), pp. 1296-1304.
Wang, et al."Transplantation of human embryonic stem cell-derived alveolar epithelial type II cells abrogates acute lung injury in mice.", Molecular Therapy: The Journal of the American Society of Gene Therapy.
Mar. 2010 LNKD—Pubmed:20087316, vol. 18, No. 3, Mar. 2010 (Mar. 2010), pp. 625-634.
Wang, et al. "A pure population of lung alveolar epithelial type II cells derived from human embryonic stem cells", Proceedings of the National Academy of Sciences of the United States of America, vol. 104, No. 11, Mar. 2007 (Mar. 2007), pp. 4449-4454.

\* cited by examiner

METHOD FOR THE PRODUCTION OF DIFFERENTIATED RESPIRATORY EPITHELIAL CELLS

CROSS-REFERENCE

This application is filed pursuant to 35 U.S.C. §371 as a United States National Phase Application of International Application Ser. No. PCT/EP2012/051818, filed Feb. 3, 2012, which claims the benefit of and the right of priority to European Patent Application No. 11000958.6 filed Feb. 7, 2011, and European Patent Application No. 11000905.7 filed Feb. 4, 2011, both of which are incorporated by reference herein in their entirety.

The present invention relates to a method for the production of differentiated respiratory epithelial cells comprising: (a) providing a cell population comprising or consisting of precursor cells of respiratory epithelial cells; (b) culturing the cell population of (a) in culture medium to which keratinocyte growth factor has been added; wherein the cultured cell population is supplemented with a glucocorticoid, a cAMP analogue and a cAMP elevating agent and wherein said supplementation is either simultaneously with the addition of keratinocyte growth factor in step (b) or prior or subsequently to the addition of keratinocyte growth factor in step (b), thereby differentiating said precursor cells into respiratory epithelial cells. The present invention further relates to the cell(s) obtained by the method of the invention for use in treating or preventing a respiratory disease and to a method for identifying a compound having a pharmacological, cytotoxic, proliferative, transforming or differentiating effect on the differentiated respiratory epithelial cells obtained by the method of the invention.

In this specification, a number of documents including patent applications and manufacturer's manuals is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The lung is constantly exposed to environmental toxins and pathogens that can destroy alveolar epithelial cells, in particular the thin injury prone AT1Cs, but also bronchial and tracheal epithelial cells, such as Clara cells and ciliated cells. The ability of the injured alveolar epithelium to quickly and efficiently self-repair is therefore very important for maintaining normal pulmonary function. Despite the endogenous repair capacity of the alveolar epithelium, it is often not sufficient. Inadequate, delayed, or impaired re-epithelialisation of the injured alveolus is regarded as a key factor in the pathogenesis of several life-threatening pulmonary diseases, including acute lung injury, acute respiratory distress syndrome, chronic obstructive pulmonary disease and hereditary surfactant deficiencies, which are caused by gene defects in three different genes—SP-B, SP-C, and ATP-binding cassette protein member A3 (ABCA3) predisposing the carrier to acute and chronic lung disease starting soon after birth. Further diseases include those affecting the bronchial epithelium, such as cystic fibrosis. Current treatments for respiratory epithelial injury and malfunction due to genetic defects at best provide symptomatic relief but offer no prospect for repair of the damaged and dysfunctional epithelium, respectfully. Thus, respiratory diseases are a major cause of mortality and morbidity worldwide.

Differentiation of specialised cells is a critical process for lung function and adaptation to physiological events, in particular during development. The respiratory epithelium is a type of epithelium found lining the entire respiratory tract comprising the airways and the alveoli. Its function is to conduct air, form a barrier to potential pathogens and foreign particles, preventing infection and tissue injury by action of the mucociliary escalator and to exchange oxygen and carbon dioxide. There are four main types of cells of the respiratory epithelium, including tracheal epithelial cells, bronchial epithelial cells, alveolar epithelial type 2 cells and alveolar epithelial type 1 cells. Development of effective pulmonary gas exchange structures and production of surfactant are necessary for successful adaptation to extrauterine life. These key processes in lung maturation require differentiation of epithelium into type 2 cells, which produce surfactant, and further differentiation into type 1 cells, which establishes the thin alveolar-capillary membrane for efficient gas exchange. Morphologically, type 2 cell differentiation is marked by the disappearance of glycogen stores, a resource for surfactant phospholipid, by formation of lamellar bodies, the intracellular storage site and secreted form of surfactant, and expansion of the apical cell surface in the form of microvilli. The major component of surfactant is disaturated phosphatidylcholine (PC), principally the dipalmitoyl species (PC16:0/16:0), which forms the surface-active film at the alveolar surface to prevent collapse of air spaces. This function requires the presence of surfactant proteins (SP), in particular SP-B and/or SP-C. Developmental regulation of the surfactant system involves transcriptional and posttranslational processes, with distinct temporal patterns for various surfactant components. In human fetal lung, mRNAs for SP-B and SP-C are first detected at ~12 wk of gestation, whereas SP-A mRNA is undetectable until 20-24 wk. Despite the relatively early appearance of SP-B/C transcripts, mature proteins that result from processing of proproteins are not found until after 20 wk of gestation. An increase in PC16:0/16:0 content in lung tissue similarly is delayed until >20 wk gestation. Infants born prematurely at 24-30 wk of gestation have a >50% risk of developing respiratory distress syndrome as a result of immaturity of lung structure and surfactant deficiency. Studies of alveolar type 2 cell differentiation in cultured fetal lung explants and in vivo indicate an important role for glucocorticoids and cAMP in the differentiation process. A limited number of glucocorticoid-regulated genes have been identified, including the SPs, lipogenic and antioxidant enzymes, insulin-like growth factor and insulin-like growth factor binding proteins, tropoelastin, and water and ion transporter/channels. Other reported regulators of lung maturation include thyroid hormones, epidermal growth factor, gastrin-releasing peptide, interleukin-1 (IL-1), and parathyroid hormone-related peptide (PTHrP).

Tracheal epithelial cells line the trachea (or windpipe) while bronchial epithelial cells play an important role as they constitute the surface epithelium of normal bronchi. Clara cells are the predominant cell type in the conducting airways of mice, being present throughout the tracheobronchial and bronchiolar epithelium, whereas in humans Clara cells only reside in the bronchiolar epithelium. In humans the predominant cell type of the conducting airways are the ciliated cells. Precursor cells for ciliated cells are basal cells as well as Clara cells. Beside a progenitor cell function, Clara cells have additional lung protective functions like detoxifying xenobiotics. Ciliated cells are crucial for the mucociliary clearance of the airways.

Winkler et al., Cloning And Stem Cells 10 (2008), 49-64 describes methods for differentiating murine embryonic stem cells towards mesendodermal progenitors using a Brachyury-eGFP knock-in mESC line. Differentiation into distal lung epithelial cells was detected using markers including SP-C that is specific for AT2 cells. In this study, replacement of serum by serum-free cultivation protocols aimed at identifying factors involved in differentiation into respiratory epithelial cells that are difficult to determine in the presence of serum components. Generally, SP-A, B and C expression was lower in samples derived from serum-free protocols as compared to protocols making use of serum components. As an activator for differentiation, activin A was used. It was found that late activin A treatment after serum activation starting at day 5 of differentiation resulted in a significantly higher SP-C expression than other serum-based differentiation based protocols. The authors conclude that there is a synergistic effect of early serum induction and late activin A treatment with respect to formation of AT2-like cells. Factors suspected to be involved in the differentiation process are factors of the fibroblast growth factor family including FGF-1, FGF-2, FGF-7, FGF-10, FGF-18 and BMP-4. The authors further assume that additional factors within fetal calf serum will promote AT2 formation and can further be identified on the basis of the protocol developed in this paper.

Roszell et al., Tissue Engineering: Part A, 15 (2009), 3351-3365 is a further study that investigated differentiation into lung alveolar epithelial type 2 (AE2) cells. In the course of their investigations, the authors found that embryonic stem cells can be differentiated in a two-step process into AE2 cells. In the first step, activin or conditioned medium from an AE2-like cell line enables direct differentiation of ESCs into endoderm cells. This differentiation process is improved by the addition of Wnt3a. The second step of differentiation into AE2-like cells is mediated by FGF-2 in a dose-dependent fashion.

Mouhieddine-Gueddiche et al., Pediatric Reseach 53 (2003), 231-239 assessed the influence of keratinocyte growth factor (KGF) and dexamethasone (Dex) on surfactant protein (SP) expression in fetal rat type 2 cells as well as cells derived from a murine lung epithelial cell line. Cells were cultured in the presence of 5% FBS. The authors found that KGF and Dex induce greater-than-additive stimulating effects on SP-A and SP-B expressions. On the other hand, these compounds provided only additive effects on SP-C expression. The synergistic activity found between KGF and Dex was attributed, at least in part, to activities at the transcriptional level. For SP-C mRNA levels, it was found that a slight decrease was observed when Dex and KGF were simultaneously present as compared to KGF presence alone. In that latter case, the level was comparable to that of the presence of Dex alone.

Berg et al., Biochem. Biophys. Res. Commun. 293 (2002) 907-912 describe that the glucocorticoid dexamethasone regulates the promoters of two genes, CCSP and CYP2B1 via C/EBP-transcription factors in lung cells. CCSP expression increased in a manner depending on the dose of glucocorticoid administered.

Gonzales et al., Am J Physiol Lung Cell Mol Physiol 283 (2002), L940-L951 describe a fully-defined culture system, with the potential exception of contaminating mesenchymal cells, for differentiation of human pulmonary type 2 cells in vitro in the presence of glucocorticoid and cAMP as well as isobutylmethylxanthine. As a source for the differentiation process, undifferentiated human fetal lung epithelial cells were used in monolayer serum-free culture serum. Culture cells exhibited typical features of alveolar type 2 cells after 4 days. In addition, the expression of a variety of genes was assessed by means of microarray analysis. Inter alia, synergistic responses for the expression of SP-B, SP-C and SP-D were observed if cAMP as well as dexamethasone were added simultaneously to the culture medium.

Sueblinvong et al., Am J Respir Crit Care Med 177, 701-711 (2008) describe that human umbilical cord blood stem cells may be used as a source to induce differentiation into airway epithelium. In their study, they assessed the expression of markers of airway epithelial phenotype including Clara cell secretory protein (CCSP) and CFTR. Among the factors used in the various growth media was KGF. However, KGF did not induce expression of differentiated lung epithelium specific markers but did induce expression of TTF-1 mRNA.

Wang et al., Molecular Therapy (2010), 1-10 describe experiments where immune-compromised SCID mice subjected to bleomycin-induced acute lung injury were transplanted with human embryonic stem cell derived-AT2 cells. It was found that AT2 cells can populate the mouse lungs and differentiate into AT1 cells. In experiments for determining the proliferation capacity of ES cell derived AT2 cells in vitro, KGF was added to some of the cultures. It was found that the addition of KGF for 7 days caused the number and size of the AT2 colonies to significantly increase. It was further found that the transplantation of AT2 cells into the lungs of mice reduced the damage effected by bleomycin. The transplanted AT2 cells further improved lung tidal volume as well as oxygen levels as compared to control mice. Finally, the transplantation resulted in normal life expectation of the previously bleomycin-treated mice. The absence of teratoma formation indicated that the AT2 cells were devoid of precursor human embryonic stem cells.

Wang et al., Am J Respir Cell Mol Biol 36 (2007), 661-668 investigated the possibility whether a system for maintaining the differentiated functions of adult human type 2 cells could be developed and whether it was possible to reverse the phenotypes of adult human type 2 cells and type 1-like cells in vitro. They found that human type 2 cells cultured on gel matrices, optionally supplemented with collagen in the presence of KGF, isobutylmethylxanthine, 8-bromo-cAMP and dexamethasone maintained the differentiated type 2 cell phenotype as measured by the expression of surfactant protein A, B, C as well as other proteins. In addition, their results show that type 2 and type 1 phenotypes can be partially reversed in vitro. As is known, type 2 cells cultured in tissue culture plastic or rat tail collagen lose markers of the type 2 phenotype and express markers of the type 1 cell phenotype. In this study, this was also found for adult human type 2 cells. Under certain culture conditions, this differentiation could be reversed in part. More specifically, the type 2 cells held in culture lose some of the markers specific for type 2 cells and regain those markers later.

Sugahara et al., Respirology 11 (2006), S28-S31 is a further document that demonstrates that KGF is a strong growth factor for alveolar type 2 cells. Specifically, KGF induced a stimulation of surfactant proteins in a dose- and time-dependent manner. In addition, it was shown that KGF prevents bleomycin-induced lung injury.

Coraux et al., Am J Respir Cell Mol Biol 32 (2005), 87-92 have shown that murine ES cells are able to differentiate into non-ciliated secretory Clara cells and that type I collagen induces this commitment. Using histological analyses, the authors showed that an epithelium generated by culturing ES cells at the air-liquid interface is composed of basal, ciliated, intermediate and Clara cells similar to those of native tracheobronchial airway eptithelium. Also assessed was the effect of KGF on ES cell cultures. KGF in addition to culture medium did not induce CC10 mRNA expression which is a Clara cell specific marker. Induction of ES cells into airway epithelial tissue was initiated by growing said ES cells as embroid bodies.

Lin et al., Experimental Lung Research 36 (2010), 307-320 analyzed the impact of various fibroblast growth factors on the development of mouse embryonic stem cells into pulmonary progenitors. Specifically, the activity of FGF-1, -2, -7 and -10 was investigated. As one read-out system, the induction of SP-C was assessed. It was found that all factors, at least at some concentrations and when given at particular stages of development, had a positive effect on the expression of markers of distal airway epithelium, sometimes, however, only when presented together with Matrigel which supposedly provides additional growth factors. Addition of FGF-7 (KGF) to a differentiation medium at an early stage did not provide any enhancement of SP-C expression whereas addition at a later stage had a positive effect.

Yano et al., Am J Physiol Lung Cell Mol Physiol 279 (2000), L1146-L1158 investigated the effect of KGF on alveolar epithelial cells. In particular, mRNA levels for SP-A, SP-B and SP-D investigated in these cells before and after treatment with KGF and were found to be changed.

Fehrenbach et al. Eur Respir J 20 (2002), 1185-1197 similarly describe a study in order to investigate the proliferative response of specific airway epithelial cell types to human KGF. The effect of human KGF was studied using two in vivo models of transiently induced pulmonary epithelial cell proliferation. The authors conclude that the potential of human keratinocyte growth factor to protect the lung against various injuries may not only rely on its effects on the alveolar epithelium but is likely to include its ability to stimulate processes implicated in airway epithelial repair, e.g. proliferation of Clara cells and increased expression of epithelial CD44v6.

Mature respiratory epithelial cells are still frequently needed for in vitro toxicology or pharmaceutical assays and also potentially for cell therapies in patients with respiratory diseases. However, lung tissues for respiratory epithelial cell isolation are rarely available. A further drawback is that those primary respiratory epithelial cells do not maintain their phenotype over time in culture. Thus, despite the fact that a lot of effort has been invested into identifying means and methods of providing differentiated respiratory epithelial cells there is still a need to provide large amounts of high quality differentiated respiratory epithelial cells for toxicological studies and clinical applications.

This need is addressed by the provision of the embodiments characterised in the claims.

Accordingly, the present invention relates in a first embodiment to a method for the production of differentiated respiratory epithelial cells comprising: (a) providing a cell population comprising or consisting of precursor cells of respiratory epithelial cells; (b) culturing the cell population of (a) in culture medium to which keratinocyte growth factor has been added; wherein the cultured cell population is supplemented with a glucocorticoid, a cAMP analogue and a cAMP elevating agent and wherein said supplementation is either simultaneously with the addition of keratinocyte growth factor in step (b) or prior or subsequently to the addition of keratinocyte growth factor in step (b), thereby differentiating said precursor cells into respiratory epithelial cells.

In accordance with the present invention, the term "respiratory epithelial cells" relates to cells having the biological function of any one of the four main types of cells of the respiratory epithelium, including tracheal epithelial cells, bronchial epithelial cells, alveolar epithelial type 2 cells and alveolar epithelial type 1 cells. In this regard, the term "differentiated" refers to partially or fully differentiated (i.e. fully mature) respiratory epithelial cells having or essentially having the biological function of one of the recited four cell types. The term "essentially having" the biological function of the recited cell types refers to at least 50% of the biological function of these cells as described elsewhere herein, such as at least 60%, at least 70%, at least 80%, at least 90%, at least 95%, at least 98% and most preferably at least 99%. It will be understood that the resulting differentiated respiratory epithelial cells have undergone differentiation (i.e. have matured) as compared to the cell population comprising or consisting of precursor cells employed to carry out the method of the invention.

As described herein above, tracheal epithelial cells line the trachea (or windpipe) while bronchial epithelial cells play an important role as they constitute the surface epithelium of normal bronchi. In mice, Clara cells are the predominant cell type in the tracheo-bronchial and bronchiolar epithelium of the conducting airways. In humans, Clara cells only reside in the bronchiolar epithelium while the predominant cell type of the conducting airways are the ciliated cells. Precursor cells for ciliated cells are basal cells as well as Clara cells. Clara cells thus have a progenitor cell function as well as additional lung protective functions like detoxifying xenobiotics. Ciliated cells are crucial for the mucociliary clearance of the airways.

The alveolar epithelium is composed of two cell types of epithelial cells, alveolar type 1 cells and alveolar type 2 cells. The majority of the surface area, more than 90% of the alveolus, is covered by the squamous alveolar type 1 cell which is a thin cell and very susceptible to injury. The other major cell type is a cuboidal cell, the alveolar type 1 cell, which comprises about 15% of the cells in the distal lung and is known primarily for its ability to synthesize, store, secrete and recycle pulmonary surfactant. Other important functions of alveolar type 2 cells are: (i) to serve as a progenitor cell for alveolar type 1 cells, particularly during re-epithelialization of the alveolus after lung injury; (ii) to transport sodium from the alveolar fluid into the interstitium so as to minimize alveolar fluid and thereby to maximize gas exchange; and (iii) to modify the inflammatory response by secreting a variety of growth factors and cytokines.

In accordance with the present invention, "alveolar epithelial type 2 cells" are characterised by the expression of the markers surfactant protein C (SP-C; which is specific for AT2 cells) and/or surfactant protein B (SP-B) and/or show a specific morphological ultra-structure when analysed with a microscope, e.g. an electron microscope characterised by a cuboidal shape in vivo, lamellar bodies as typical organelles and/or micro-villi. Further, "alveolar epithelial type 1 cells", in accordance with the present invention, are characterised by the expression of the marker proteins aquaporin 5 and/or T1 alpha and/or are characterised morphologically by a squamous shape, microvilli and/or organelles associated with metabolic functions such as mitochondria, abundant smooth and/or rough endoplasmic reticulum and/or Golgi apparatus when analysed with a microscope, e.g. an electron microscope.

"Bronchial epithelial cells", such as for example Clara cells are characterised by the expression of the marker proteins clara cell secretory protein (CCSP), surfactant protein B (SP-B) and/or cytochrome P450 enzymes and/or morphological characteristics including a dome-shape, the presence of microvilli and/or smooth endoplasmic reticulum.

Ciliated cells as an example of "tracheal epithelial cells", but also "bronchial epithelial cells" are characterised by the expression of the marker proteins β-tubulin 4 and/or Foxj1 (also referred to as HFH-4 in the literature) and/or the presence of cilia as evident by microscopic analysis.

It is understood by the person skilled in the art that the above described morphological factors vary dependent on the culture surroundings of the cells. Thus, when grown in vitro the shape of the cells might be similar but not identical to cells grown in the context of a physiological environment including naturally occurring neighbouring cells. Thus, when characterising the differentiated respiratory epithelial cells of the present invention, the expression of marker proteins serves as a primary characteristic while the morphological characteristics serve as secondary markers. The skilled person knows how to compare the shape of a cell obtained by the method of the present invention with a naturally occurring respiratory epithelial cells, for example by isolating respiratory epithelial cells obtained from a biopsy and/or by culturing said cells in vitro for comparison.

In accordance with the invention the term "precursor cell" refers to a cell having the capability to differentiate into a mature cell, e.g. into a mature respiratory epithelial cell in accordance with the method of the invention. Thus, a precursor cell specifies a cell which is partially or fully undifferentiated. With regard to the present invention, the precursor cell is a partially differentiated cell or a fully undifferentiated cell and has the capability to differentiate into a cell having a mature respiratory epithelial cell phenotype. Precursor cells, in accordance with the present invention, thus encompass stem cells, such as e.g. embryonic stem cells, adult stem cells, germline-derived stem cells or induced pluripotent stem cells but also partially reprogrammed cells.

The term "stem cells", in accordance with the present invention, relates to a cell type having the capacity for self-renewal, an ability to go through numerous cycles of cell division while maintaining the undifferentiated state, and the potential of differentiation, i.e. the capacity to differentiate into specialized cell types. Preferably, the stem cells according to the present invention are totipotent or pluripotent stem cells, i.e. they can differentiate into all embryonic and extra-embryonic cell types or the stem cells are multipotent and can differentiate into various specific cell types, including respiratory epithelial cells, but not all cell types. The term stem cells encompasses embryonic stem cells as well as adult stem cells. The term "embryonic stem cells", as used throughout the present invention, refers to stem cells derived from the inner cell mass of an early stage embryo known as a blastocyst.

Embryonic stem (ES) cells are pluripotent, i.e. they are able to differentiate into all derivatives of the three primary germ layers: ectoderm, endoderm, and mesoderm. Recent advances in embryonic stem cell research have led to the possibility of creating new embryonic stem cell lines without destroying embryos, for example by using a single-cell biopsy similar to that used in preimplantation genetic diagnosis (PGD), which does not interfere with the embryo's developmental potential (Klimanskaya et al. (2006)). Furthermore, a large number of established embryonic stem cell lines are available in the art (according to the U.S. National Institutes of Health, 21 lines are currently available for distribution to researchers), thus making it possible to work with embryonic stem cells without the necessity to destroy an embryo.

Adult stem cells are undifferentiated cells, found throughout the body after embryonic development, that multiply by cell division to replenish dying cells and regenerate damaged tissues. They can be found in juvenile as well as adult animals and humans. Non-limiting examples of adult stem cells include hematopoietic stem cells, mammary stem cells, mesenchymal stem cells, endothelial stem cells, neural stem cells, neural crest stem cells, olfactory adult stem cells and testicular cells.

In a preferred embodiment, the stem cells are human stem cells. More preferably, the human stem cells are human embryonic stem cells. It is preferred that the human stem cells or human embryonic stem cells are obtained by methods that do not involve the destruction of a human embryo, such as for example the above described methods of using a single-cell biopsy or by employing an established cell line.

"Germline-derived stem cells", in accordance with the present invention, relate to stem cells obtained from germ cells, including embryonic germ-cells, parthenogenetic embryonic stem cells as well as multipotent adult germline stem cells from e.g. testis or ovaries (Guan et al. (2006), Nature 440: 1199-1203; Revazova et al. (2007), Cloning and Stem Cells 9: 432-449; Matsui et al. (1991), Nature 353: 750-752; Resnick et al. (1992), Nature 359: 550-551).

"Parthenogenetic stem cells" in accordance with the present invention, are embryonic stem cells isolated from the blastocyst stage of parthenogenetic embryos. Parthenogenetic embryos are produced by parthenogenetic (i.e. asexual) activation of non-fertilised oocytes.

"Induced pluripotent stem cells", in accordance with the present invention, are pluripotent stem cells derived from a non-pluripotent cell, typically an adult somatic cell, by inducing a "forced" expression of certain genes. Induced pluripotent stem cells are identical to natural pluripotent stem cells, such as e.g. embryonic stem cells, in many respects including, for example, the expression of certain stem cell genes and proteins, chromatin methylation patterns, doubling time, embryoid body formation, teratoma formation, viable chimera formation, and potency and differentiability (Takahashi and Yamanaka 2006, Cell 126: 663-676). Induced pluripotent stem cells are an important advancement in stem cell research, as they allow researchers to obtain pluripotent stem cells without the use of embryos (Nishikawa et al., 2008). The induced pluripotent stem cells may be obtained from any adult somatic cell, preferably from fibroblasts, such as for example from skin tissue biopsies.

Methods for the generation of human induced pluripotent stem cells are well known to the skilled person. For example, induced pluripotent stem cells can be generated from human skin tissue biopsies (Park and Daley, 2009; Park et al., 2008). Fibroblasts are grown in MEM-medium containing chemically defined and recombinant serum components. For reprogramming, the human fibroblasts are retrovirally transduced with OCT4, SOX2, c-MYC and NANOG genes. For this, genes are cloned into a retroviral vector and transgene-expressing viral particles are produced in the HEK293FT cell line. Human skin fibroblasts are co-transduced with all four vectors. The obtained iPS cells are cultured according to protocols established for human embryonic stem cells in DMEM-medium containing serum replacement factors and recombinant growth factors. The iPS cells are analyzed for normal morphology and normal karyotype and are studied by fingerprinting analysis and immunostaining for OCT3/4, NANOG, SSEA-3, SSEA-4, Tra-1-60 and Tra-1-81. Gene transcripts for OCT4, SOX2, NANOG, KLF4, c-MYC, REX1, GDF3 and hTERT are analyzed by real-time RT-PCR. Furthermore, multilineage differentiation of iPS cells is confirmed by embryoid body, teratoma formation and differentiation into adult cell types (Choi et al., 2009; Zhang et al., 2009). As another example, human IFS cells can also be obtained from embryonic fibroblasts without viral integration using adenoviral vectors expressing c-Myc, Klf4, Oct4, and Sox2 (Zhou and Freed, 2009). Further methods are described e.g. in WO2009115295, WO2009144008 or EP2218778.

In accordance with the present invention, "partially reprogrammed cells" are precursor cells derived from somatic cells by trans-differentiation, wherein the cells have a precursor phenotype of respiratory epithelial cells but are not pluripotent. For partially reprogrammed cells, the conventional reprogramming towards pluripotency through overexpression of e.g. Oct4, Sox2, Klf4 and c-Myc as employed for the generation of induced pluripotent stem cells is shortcut and the reprogramming is directed towards the desired cell type precursor in a fast and efficient manner. This method has been described in the art, e.g. for the trans-differentiation of cardiomyocytes (Efe et al. (2011), Nature cell biology DOI: 10.1038/ncb2164).

The precursor cells of the invention may be obtained from a subject or derived from a cell line. The term "subject" as used herein means a vertebrate, preferably a mammal, more preferably any one of cat, dog, horse, cattle, swine, goat, sheep, mouse, rat, monkey, ape and human, and most preferably a human.

The term "keratinocyte growth factor", (also referred to as fibroblast growth factor-7 in the art), as used herein, refers to a protein that in humans is encoded by the FGF7 gene. The protein encoded by this gene is a member of the fibroblast growth factor (FGF) family. FGF family members possess broad mitogenic and cell survival activities, and are involved in a variety of biological processes, including embryonic development, cell growth, morphogenesis, tissue repair, tumor growth and invasion. Keratinocyte growth factor (also referred to as KGF herein) is a potent epithelial cell-specific growth factor, whose mitogenic activity is predominantly exhibited in keratinocytes but not in fibroblasts and endothelial cells. Human KGF has the Gene ID: 2252 and REF-SEQ accession number NM_002009.3. Preferred amounts of keratinocyte growth factor to be employed are between 0.01 and 10.000 ng/ml, preferably between 0.1 and 1000 ng/ml, more preferably between 1 and 100 ng/ml, even more preferably between 5 and 50 ng/ml, such as for example between 10 and 30 ng/ml, such as between 15 and 25 ng/ml and most preferably the amount is 20 ng/ml.

The addition of keratinocyte growth factor in step (b) initiates a differentiation process towards mature respiratory epithelial cells. Depending on the cell type provided in step (a) it is understood by the skilled person that the addition of keratinocyte growth factor can initiate differentiation, e.g. in cases where fully un-differentiated cells are employed as the starting material, or may advance the differentiation of partially differentiated cells, such as e.g. partially reprogrammed cells. Also encompassed by the method of the invention is that un-differentiated cells, such as e.g. embryonic stem cells, are cultured in a differentiation medium and keratinocyte growth factor is added after a period of time such as for example at least one day, at least two days, at least three days, at least four days or at least five days after initiating differentiation. Most preferably, keratinocyte growth factor is added at the beginning of the culture of step (b), i.e. on day 0 simultaneously with the transfer of cells to the culture medium or with changing the culture medium. The beginning of the cell culture in step (b) may coincide with step (a) in those embodiments where cells are provided but not cultured prior to the cell culture step of (b). Standard differentiation media for stem cells are well known in the art and exemplary media are further described in the appended examples.

In accordance with the present invention, the term "glucocorticoid" relates to a class of steroid hormones that bind to the glucocorticoid receptor. They play a part in the regulation of a wide range of physiological and pathophysiological processes including, metabolism, immune response, development, cognition and arousal. Activation of the glucocorticoid receptor complex up-or downregulates the expression of many proteins that mediate these processes. Binding of glucocorticoids to their cognate receptors evokes a translocation of the receptor from the cytosol into the nucleus, enabling the receptor to bind to and activate target genes. Examples of glucocorticoids include, without being limiting, cortisol (also referred to as hydrocortisone) and corticosterone, with cortisol being the most important human glucocorticoid. Various synthetic glucocorticoids are available, such as for example dexamethasone, prednisone, prednisolone, betamethasone or triamcinolone. Preferred amounts of glucocorticoid to be employed are between 0.01 and 10.000 nM, preferably between 0.1 and 1000 nM, more preferably between 1 and 100 nM, even more preferably between 5 and 50 nM, such as for example between 10 and 30 nM, such as between 15 and 25 nM and most preferably the amount is 10 nM.

The term "cAMP analogue", in accordance with the present invention relates to chemical compounds with biological properties similar to cAMP. Non-limiting examples of cAMP analogues include any compound having the following formula and comprising modifications of the moieties highlighted in grey boxes, such as for example 8-bromo-cAMP, dibutyryl-cAMP or 8-chloro-cAMP.

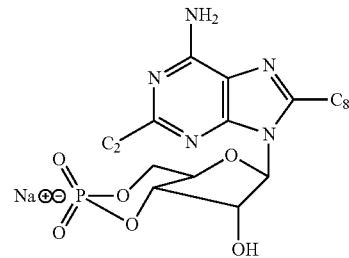

Preferred amounts of cAMP analogue to be employed are between 0.0001 and 100 mM, preferably between 0.001 and 10 mM, more preferably between 0.01 and 1 mM, even more preferably between 0.05 and 0.5 mM, and most preferably is 0.1 mM.

In accordance with the present invention, the term "cAMP elevating agent" relates to compounds capable of increasing the intracellular level of cAMP. The level of intracellular cAMP is increased when a higher amount, such as for example at least 10% more, such as at feast 20% more, such as at least 30% more, such as at least 50% more, such as at least 75% more, such as at least 100% more, such as at least 1000% more cAMP is present in a cell that has been contacted with the compound as compared to a cell not contacted with the compound. An increase in intracellular cAMP levels can be achieved for example by inhibition of the activity of phosphodiesterase and/or by activating adenylate cyclase. Non-limiting examples of cAMP elevating agents include isobutylmethylxanthine or forskolin. Preferred amounts of cAMP elevating agent to be employed are between 0.0001 and 100 mM, preferably between 0.001 and 10 mM, more preferably between 0.01 and 1 mM, even more preferably between 0.05 and 0.5 mM, and most preferably is 0.1 mM The term "wherein the cultured cell population is supplemented with a glucocorticoid, a cAMP analogue and a cAMP elevating agent and wherein said supplementation is either simultaneously with the addition of keratinocyte growth factor in step (b) or prior or subsequently to the addition of keratinocyte growth factor in step (b)" refers to either (i) culturing the cell population (such as a stem cell population) in the presence of keratinocyte growth factor, a glucocorticoid, a cAMP analogue and a cAMP elevating agent at the same time, such as for example upon initiating the differentiation process or (ii) culturing the cell population first with the glucocorticoid, the cAMP analogue and the cAMP elevating agent (added as a combination together or added subsequently to each other) and adding keratinocyte growth factor at a later time point to said cell culture, such as for example some hours or days or even weeks later or (iii) culturing the cell population first with keratinocyte growth factor and adding the glucocorticoid, the cAMP analogue and the cAMP elevating agent (as a combination together or subsequently to each other) at a later time point to said cell culture, such as for example some hours or days or even weeks later. Also encompassed by this embodiment is that the cell population is cultured first with one or two of the factors selected from the group consisting of a glucocorticoid, a cAMP analogue and a cAMP elevating agent, then at a later time point (such as for example some hours or days or even weeks later) the cells are further cultured in the additional presence of keratinocyte growth factor and at the same time or at an even later time point (such as for example some hours or days or even weeks later) the cells are further cultured in the additional presence of the remaining one or two factors selected from the group consisting of a glucocorticoid, a cAMP analogue and a cAMP elevating agent. For example, the cells may be cultured in the presence of a glucocorticoid, followed by a further culture period in the presence of said glucocorticoid and keratinocyte growth factor, followed by a further culture period in the presence of all four factors.

Most preferably, the cultured cell population is supplemented with a glucocorticoid, a cAMP analogue and a cAMP elevating agent either simultaneously with the addition of keratinocyte growth factor in step (b) or subsequently to the addition of keratinocyte growth factor in step (b).

Preferably, addition of glucocorticoid, cAMP analogue and cAMP elevating agent at a later time point is carried out about 5 days after addition of keratinocyte growth factor, such as for example about 10 days after addition of keratinocyte growth factor, such as for example about 12 days after addition of keratinocyte growth factor and most preferably about 14 days after addition of keratinocyte growth factor. The addition of glucocorticoid, cAMP analogue and cAMP elevating agent may also be carried out about 17 days after addition of keratinocyte growth factor, such as for example about 21 days after addition of keratinocyte growth factor. Preferably, the glucocorticoid, cAMP analogue and cAMP elevating agent are added essentially simultaneously to the culture.

The method of the invention, in particular step (b), is carried out under suitable cell culture conditions. It is of note that general cell culture conditions are well known in the art (e.g. Cooper G M (2000). "Tools of Cell Biology", ISBN 0-87893-106-6; K. Turksen, ed., Humana Press, 2004, "Adult stem cells" ISBN-10 1-58829152-9, J. Masters, ed., Oxford University Press, 2000, "Animal cell culture", ISBN-10 0-19-963796-2). Suitable culture conditions are for example shown in more detail in the Examples of the invention. Appropriate media include for example Iscove's Modified Dulbecco's Medium.

It was surprisingly discovered in accordance with the present invention that an even earlier developmental stage as investigated in the prior art could be used as a starting point to induce differentiation into respiratory epithelial cells. In particular, it was unexpectedly found that the highest expression of the alveolar epithelial type 2 (AT2) cell-specific marker surfactant protein C (SP-C) was observed when keratinocyte growth factor (KGF) supplementation had started already on day 0 of differentiation compared to later KGF supplementation. This result cannot solely be explained by a proliferation/maturation effect, but rather by an additional effect of KGF on the generation of lung epithelial (progenitor) cells from pluripotent stem cells per se during the early phase of differentiation when lung epithelial cells are not yet originated. Similar to KGF glucocorticoids have a stimulating effect on the maturation of primary lung epithelial cells[7, 8]. It has been shown that the effect of glucocorticoids is even potentiated by the simultaneous addition of a cAMP analog and isobutylmethylxanthine[8]. In line with these observations on primary lung epithelial cells, the addition of the three factor combination glucocorticoid, 8-bromo-cAMP and isobutylmethylxanthine (DCI) to differentiating pluripotent stem cells resulted in an enhanced SP-C expression versus basal medium alone with the highest expression following supplementation starting on day 10/14 (FIG. 1A). In particular the combination of KGF (day 0-24) and DCI led to a significant increase of SP-C expression compared to basal medium alone with the highest expression following DCI supplementation starting on day 14 (53-fold increase vs. BM). Moreover, the combination of KGF (d0-24) and DCI (day 14-24) also accelerated the expression of surfactant protein B (SP-B; 11-fold increase vs. BM; FIG. 1B), a marker of alveolar epithelial AT2 and bronchial/bronchiolar epithelial Clara cells, and the expression of Clara cell secretory protein (CCSP; 4-fold increase vs. BM; FIG. 1C), a marker of Clara cells. Although, a synergistic effect of KGF+DCI on the proliferation/maturation of primary AT2 cells has already been shown[9], we were able to newly discover a synergistic inducing effect of an early application of KGF plus glucocorticoids, a cAMP analog and isobutylmethylxanthine on the differentiation of alveolar and bronchial/bronchiolar epithelial cells from pluripotent stem cells as exemplarily shown by the combination of KGF (d0-24) and DCI (d14-24). Electron microscopy was used to detect cells with an ultrastructure typical for lung epithelial cells. Differentiation cultures harvested at the end of differentiation on day 24 and treated with KGF (day 0-24) and DCI (day 14-24) contained lung-like epithelium with a clear basal to apical orientation (FIG. 2A). Cells were visible with microvilli at their apical side, typical for AT2 cells. In addition, these cells contained electron-dense organelles with a lamellar structure, the so called lamellar bodies, which are typical organelles of AT2 cells. These lamellar bodies had the most similarity to that of mature primary AT2 cells compared to any detected lamellar body-like structure in former studies. In conclusion, electron microscopy measurements confirmed the presence of lung epithelial cells developed in pluripotent stem cell differentiation cultures following treatment with KGF and DCI.

As has been discussed by Gonzales and colleagues (ibid.), it could not be assumed a priori that agents capable of inducing differentiation in intact tissue and maintaining differentiated function of cultured mature type 2 cells would necessarily be sufficient for inducing differentiation of immature fetal lung epithelial cells. The same holds true for findings of the underlying invention. More specifically, the fact that combinations of factors that can be subsumed under the present invention have been shown in the art to maintain alveolar type 2 cell phenotypes or even assist differentiation of alveolar type 2 cells into alveolar type 1 cells can by no means be considered as predictive for assisting or mediating the differentiation of stem cells such as embryonic stem cells or induce pluripotent stem cells into respiratory epithelial cells. Furthermore, the use of materials derived from animals can be circumvented by the provision of the defined culture conditions described by the present invention, thus providing significant advantages for the potential therapeutic use in humans.

In a preferred embodiment, the method of the invention further comprises identifying and optionally isolating the respiratory epithelial cells produced.

Methods of identifying respiratory epithelial cells are well known in the art and include, without limitation, morphological identification based on cell shape as described herein above as well as identification based on molecular markers specifically expressed by respiratory epithelial cells. Such markers have also been described herein above and can serve to distinguish the differentiated respiratory epithelial cells from the immature or completely un-differentiated cell population, such as e.g. a stem cell population.

In accordance with the present invention, the term "isolating" refers to a selective accumulation of the produced respiratory epithelial cells. Preferably, populations of isolated cells comprise at least 70% of respiratory epithelial cells. More preferably, at least 80%, such as at least 90%, at least 95%, at least 98%, such as at least 99% and most preferably 100% of the cell population are respiratory epithelial cells.

Isolation of respiratory epithelial cells may be achieved by any method known in the art. For example, respiratory epithelial cells possess a specific morphology such that these cells can be distinguished from non-lung epithelial cells, in particular form the starting cell culture comprising or consisting of e.g. immature cells or undifferentiated or partially differentiated stem cells, by their cellular body. Therefore, respiratory epithelial cells can be identified by their morphology and can be mechanically isolated and transferred to a solid support, such as for example a different cell culture dish or flask. Mechanical isolation relates to the manual selection and isolation of cells, preferably under a microscope and may be performed by methods known in the art, such as for example aspiration of the cells into the tip of pipette or detaching of the cells using a cell scraper or density gradient centrifugation (Kamihira and Kumar, 2007).

As an alternative exemplary method of isolating respiratory epithelial cells, the cells may be subjected to methods such as e.g. cell sorting approaches including for example magnetic activated cell sorting (MACS) or flow cytometry activated cell sorting (FACS), panning approaches using immobilised antibodies, high-throughput fluorescence microscopy or the use of density gradients. Any surface protein expressed, preferably selectively expressed (i.e. not expressed or not expressed to a significant amount on other cell types present in the culture), on respiratory epithelial cells as described herein above may be employed for this isolation. Such methods are known to the person skilled in the art and have been described, for example in Dainiak et al., 2007.

In another preferred embodiment of the method of the invention, the precursor cells of differentiated respiratory epithelial cells are stem cells, such as e.g. embryonic stem cells, adult stem cells, germline-derived stem cells or induced pluripotent stem cells or are partially reprogrammed cells. Most preferably, the precursor cells of differentiated respiratory epithelial cells are embryonic stem cells, adult stem cells or induced pluripotent stem cells.

In a further preferred embodiment of the method of the invention, the respiratory epithelial cells are selected from the group consisting of bronchial epithelial cells, alveolar epithelial type 2 cells, alveolar epithelial type 1 cells and tracheal epithelial cells.

Bronchial epithelial cells, alveolar epithelial type 2 cells, alveolar epithelial type 1 cells and tracheal epithelial cells are defined as described herein above.

In another preferred embodiment of the method of the invention, the glucocorticoid is dexamethasone.

Dexamethasone is well known in the art and has the formula:

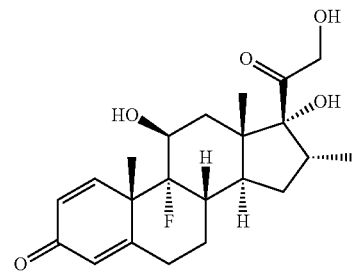

In a further preferred embodiment of the method of the invention, the cAMP analogue is 8-bromo-cAMP or dibutyryl-cAMP. Most preferably, the cAMP analogue is 8-bromo-cAMP.

In another preferred embodiment of the method of the invention, the cAMP elevating agent is isobutylmethylxanthine or forskolin. Most preferably, the cAMP elevating agent is isobutylmethylxanthine.

"Isobutylmethylxanthine" is a non-specific inhibitor of phosphodiesterases, which also possesses adenosine antagonist activity, and has the formula:

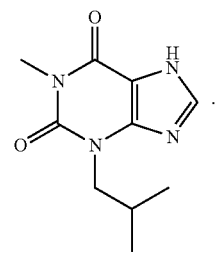 [SMILES: CC(C)Cn1c(=O)n(C)c(=O)c2[nH]cnc21]

In another preferred embodiment of the method of the invention, the cell population is cultured in suspension.

The term "cultured in suspension" as used herein refers to the culture of cells such that the cells do not adhere to the solid support or the culture vessel. To transfer cells into a suspension culture, they are for example removed from the culture dish by a cell scraper and transferred to sterile dishes (e.g. bacterial dishes) containing culture medium, which do not allow adhesion of the cells to the surface of the dish.

Thus, the cells are cultured in suspension without adherence to a matrix or the bottom of the dish. Alternatively, and as described in the appended examples, cells may be grown by the so-called hanging drop method, such as for example described in Winkler et al. 2008[3].

The culture of the cell population, in particular of stem cells, in a suspension culture results in the formation of cell aggregates. Where stem cells are employed, these aggregates are also referred to as "embryoid bodies". Cell aggregates, such as embryoid bodies, are generally comprised of a large variety of differentiated cell types, as upon aggregation differentiation is typically initiated and the cells begin to a limited extent to recapitulate embryonic development.

In another preferred embodiment of the method of the invention, the cell population is cultured as adherent cell culture.

In accordance with this embodiment, the entire cell culture is carried out as adherent cell culture, thus omitting the step of aggregate-formation in a suspension culture.

"Adherent cell culture", as used herein, refers to a method of culture wherein the cells adhere to the solid support. Methods of growing cells as adherent culture are well known in the art. When grown as adherent cell culture, the cells may grow as monolayers, single cells or cell clusters.

The term "solid support", in accordance with the present invention, refers to a surface enabling the adherence of cells thereto. Said surface may be, for example, the wall or bottom of a culture vessel, a plastic or glass slide such as for example a microscope slide or (a) bead(s) offering a surface for adherence. Conditions suitable to allow attachment of the cells are also well known to the skilled person and have been described, for example, in Schmitz, 2009. Preferably, said conditions are achieved by coating the solid support with an agent that enhances attachment of cells to the solid support. Such coating agents as well as methods of using them are also well known in the art and include, without being limiting, gelatine and fibronectin as for example described in the examples below, but also poly-L-lysin, poly-L-ornithin, collagen, tenascin, perlecan, phosphocan, brevican, neurocan, thrombospondin and laminin.

It is to be understood that following the growth in suspension and the formation of aggregates, the cells can optionally further be grown as an adherent cell culture.

It is further envisaged in accordance with the present invention that the cell culture is carried out as a co-culture with e.g. isolated lung tissue. For co-cultivation, the cells are brought into direct or indirect (e.g. separation by a filter membrane) contact with said isolated lung tissue. It will be understood that said co-cultivation may be carried out at any step of the method of the invention, i.e. directly from the beginning of the differentiation process (e.g. in step (a) or at the time of initiating step (b)) or at any time during said differentiation process (e.g. during step (b)). Methods for carrying out such co-cultures are well known in the art and have been described, for example, in Van Vranken (2005, Tissue Eng) or Denham (2007, Am J Physiol Lung Cell Mol Physiol).

In addition, it is also envisaged in accordance with the present invention that the cells are incorporated into isolated lungs and cultured therein. Thus, isolated lungs are provided, such as e.g. fetal murine lungs, and the cells are incorporated, e.g. injected, into said isolated lungs and cultured therein.

Furthermore, the present invention further envisages that the stem cells are cultured as tissue engineered constructs or in tissue engineered constructs. "Tissue engineered constructs", as used herein, refers to 3D structures of biological or artificial matrices seeded with the cell population in accordance with the method of the present invention.

In another preferred embodiment of the method of the invention, the cell population comprising or consisting of precursor cells is selected from a human cell population, a mouse cell population, a monkey cell population and a porcine cell population.

In another preferred embodiment of the method of the invention, the culturing of stem cells is in serum-free medium.

In accordance with this embodiment, at least a part of the cell culture (i.e. certain time periods) are carried out in serum-free medium. For example, medium containing serum may be exchanged for serum-free medium around day 1, day 2, day 3, day 4, day 5, day 6, day 7, day 8, day 9, day 10, day 11, day 12, day 13, day 14, day 15, day 16, day 17, day 18, day 19, day 20, day 21, day 22, day 23, day 24 etc of the cell culture. Alternatively, the entire differentiation cell culture process may be carried out in the absence of serum. Means of culturing cells in serum-free medium are well established in the art and include, without being limiting, the culture of cells in the presence of serum replacement.

In another preferred embodiment of the method of the invention, the cells obtained are essentially free of pathogens, more preferably the cells are free of pathogens. Such pathogens are well known to the skilled person and include, without being limiting, viruses such as for example Hepatitis virus A, B, C, Epstein-Barr-Virus or HIV-Virus and bacteria such as for example *mycoplasm* or *chlamydia*.

In a further preferred embodiment of the method of the invention, the differentiated respiratory epithelial cells are characterized by at least one of (a) the expression of surfactant protein C (SP-C) and/or surfactant protein B (SP-B) and/or a cuboidal shape in vivo, lamellar bodies and/or micro-villi for alveolar epithelial type 2 cells; (b) the expression of aquaporin 5 and/or T1alpha and/or a squamous shape for alveolar epithelial type 1 cells; (c) the expression of clara cell secretory protein (CCSP), and/or surfactant protein B (SP-B) and/or cytochrome P450 enzymes and/or a dome-shape, microvilli and/or smooth endoplasmic reticulum for bronchial epithelial cells, such as for example Clara cells; and (d) the expression of β-tubulin 4 and/or Foxj1 and/or the presence of cilia for tracheal and bronchial epithelial cell types such as ciliated cells.

These characteristics of respiratory epithelial cells have been described herein above.

The present invention further relates to the cell(s) obtained by the method according to the invention for use in treating or preventing a respiratory disease.

Accordingly, also described herein is a method of treating or preventing a respiratory disease comprising administering a pharmaceutically effective amount of cells obtained by the method according to the invention to a subject in need thereof.

Moreover, described herein is a method of treating or preventing a respiratory disease in a subject in need thereof comprising (a) isolating a cell population comprising precursor cells of differentiated respiratory epithelial cells, wherein said cell population is isolated from said subject; (b) differentiating the precursor cells of the cell population into mature (i.e. differentiated) respiratory epithelial cells by culturing the cell population of (a) in culture medium to which keratinocyte growth factor has been added; wherein the cultured cell population is supplemented with a glucocorticoid, a cAMP analogue and a cAMP elevating agent and wherein said supplementation is either simultaneously with the addition of keratinocyte growth factor in step (b) or prior or subsequently to the addition of keratinocyte growth factor in step (b); and (c) administering a pharmaceutically effective amount of said differentiated cells obtained in (b) to said subject.

As shown in the examples of the application, the cells obtained by the method of the invention have the phenotype similar to mature respiratory epithelial cells. Thus, it can be expected that these cells can substitute or partly substitute for mature respiratory epithelial cells in vivo, in particular when used for the treatment or inhibition of a respiratory disease as defined herein.

The term "respiratory disease" as used herein refers to any pathological condition or injury involving the loss of respiratory epithelial cells, or the dysfunction/loss of function of respiratory epithelial cells. Thus, the cells obtained by the method of the invention are capable to supplement or partially supplement for mature respiratory epithelial cells and/or the function of mature respiratory epithelial cells. Respiratory diseases comprise but are not limited to acute lung injury, acute respiratory distress syndrome, chronic obstructive pulmonary disease, bronchopulmonary dysplasia, cystic fibrosis, surfactant deficiencies and bronchiolitis obliterans.

In another embodiment the invention relates to a method for identifying a compound having a pharmacological, cytotoxic, proliferative, transforming or differentiating effect on the differentiated respiratory epithelial cells obtained by the method of the invention, comprising: (a) contacting the differentiated respiratory epithelial cells obtained by the method of the invention with a test compound; and (b) determining whether the test compound has one or more of said effects on said differentiated respiratory epithelial cells.

The differentiated respiratory epithelial cells obtained by the method described herein are suitable for pharmacological or scientific research and may replace testing of cells directly obtained from lung and/or animal experiments. In this regard, compounds may be tested with regard to their effect on differentiated respiratory epithelial cells that have been obtained by the method of the invention. Such effects comprise pharmacological, cytotoxic, proliferative, transforming or differentiating effect. Such effects may be for example monitored by measuring cell proliferation, apoptosis, cell morphology, cell migration, gene expression, cellular protein, or metabolic processes.

In an alternative embodiment, the invention relates to a method for the production of differentiated respiratory epithelial cells comprising: (a) providing a cell population comprising or consisting of precursor cells of respiratory epithelial cells; (b) culturing the cell population of in culture medium to which keratinocyte growth factor has been added; wherein the cultured cell population is supplemented with at least two agents selected from the group consisting of: a glucocorticoid, a cAMP analogue and a cAMP elevating agent and wherein said supplementation is either simultaneously with the addition of keratinocyte growth factor in step (b) or prior to or subsequently to the addition of keratinocyte growth factor in step (b), thereby differentiating said precursor cells into respiratory epithelial cells.

Thus, envisaged are a combination of keratinocyte growth factor with: (i) a glucocorticoid and a cAMP analogue; (ii) a glucocorticoid and a cAMP elevating agent and (iii) a cAMP analogue and a cAMP elevating agent. Again, the glucocorticoid, cAMP analogue and/or cAMP elevating agent, either in combination or separately, i.e. subsequently to each other, may be administered simultaneously with the keratinocyte growth factor or prior or subsequently thereto.

All the definitions and preferred embodiments described herein with regard to the first embodiment apply mutatis mutandis also to this embodiment.

Unless otherwise defined, all technical and scientific terms used herein have the same meaning as commonly understood by one of ordinary skill in the art to which this invention belongs. In case of conflict, the patent specification, including definitions, will prevail.

The figures show:

FIG. 1: KGF and DCI induce marker expression of lung epithelial cells like AT2 and Clara cells in pluripotent stem cell-differentiation cultures. Depicted is the mean±SD (n=3-13) of the relative marker mRNA expression (normalized to the mRNA expression of β-actin) in day 24 differentiation cultures. BM=basal medium without growth factors, DCI=dexamethasone, 8-bromoadenosine-cAMP and isobutylmethylxanthine, KGF=keratinocyte growth factor. *p<0.05, p<0.01, *p<0.001.

Figure 2:
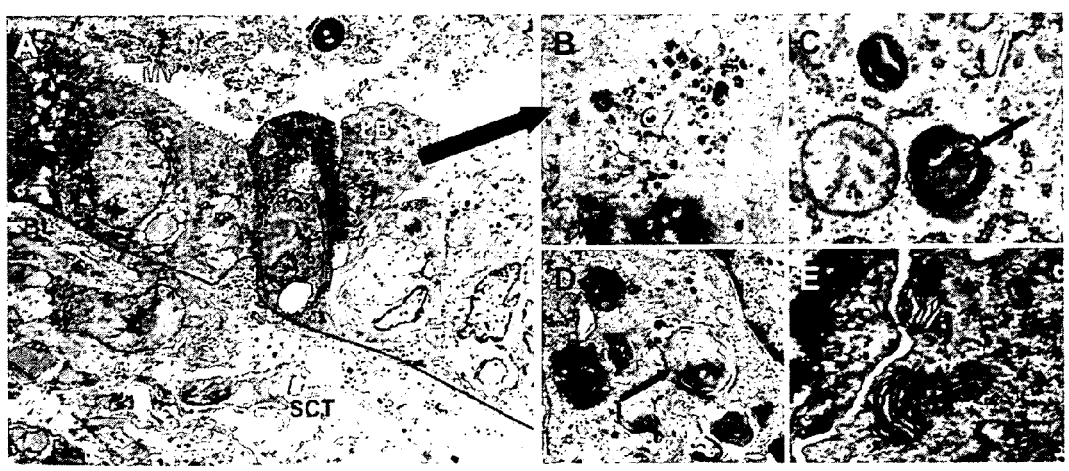

FIG. 2: Day 24 differentiation cultures treated with KGF and DCI contain lung-like epithelial ultrastructures. A: Lung-like epithelium with a basal to apical orientation. B=magnification of a cell with a cluster of electron-dense lamellar bodies in picture A (arrow), C-E: Different stages of lamellar bodies (arrows). BM=basal lamina; LB=lamellar bodies; MV=microvilli; SCT=subepithelial connective tissue, TJ=tight junction.

Figure 3:
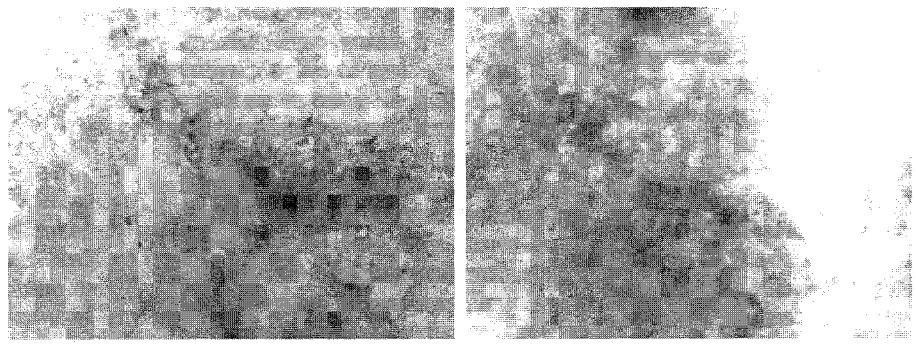

FIG. 3: Different foci of fixed CCSP-lacZ expressing bronchial/bronchiolar epithelial cells (blue) stained with X-gal.

Figure 4:
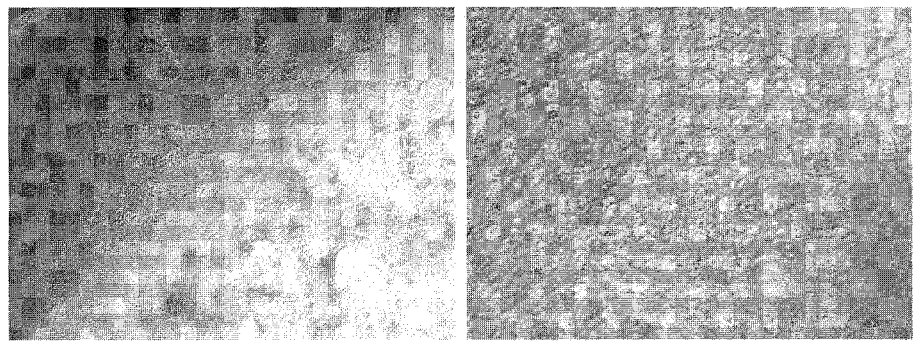

FIG. 4: Different foci of living CCSP-lacZ expressing bronchial/bronchiolar epithelial cells (green) stained with ImaGene Green™.

Figure 5:
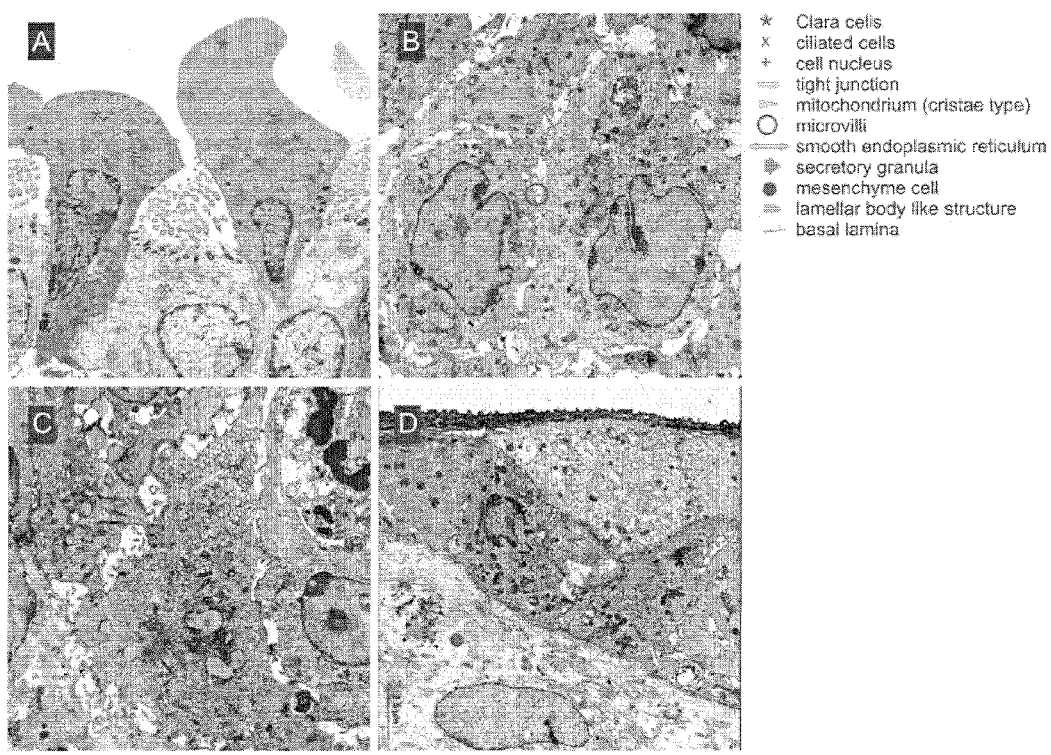

FIG. 5: Electron microscopy demonstrates the Clara cell phenotype of CCSP-lacZ positive cells. The ultrastructure of the generated Clara cells (B-D) is highly similar to native Clara cells (A).

The examples illustrate the invention:

Example 1: Pluripotent Stem Cell Lines

A transgenic murine Brachyury-GFP/Foxa2-CD4 embryonic stem (ES) cell line[1] (kindly gift of Paul Gadue and Gordon Keller) was used which enables the monitoring and optimization of mesendodermal progenitor cell generation from which lung epithelial cells develop.

Embedded in a funded project (CARPuD, BMBF) fibroblasts from transgenic CCSP-rtTA/tetO-lacZ mice, which express β-galactosidase/lacZ driven by the Clara cell secretory protein (CCSP) promoter in the presence of doxycycline, were reprogrammed into induced pluripotent stem (iPS) cells based on established protocols[2]. This CCSP-rtTA/tetO-lacZ iPS cell line was used for the monitoring and visualization of bronchial/bronchiolar epithelial differentiation from iPS cells.

Example 2: Cultivation of Pluripotent Stem Cells

Pluripotent stem cells were routinely cultured on mitotically inactivated murine embryonic fibroblasts (MEFs). The culture medium for "undifferentiated cells" was composed of Dulbecco's Modified Eagle's Medium (Invitrogen) supplemented with 15% fetal calf serum (FCS; Thermo Scientific), 0.2 mM L-glutamine (Invitrogen), 0.1 mM β-mercaptoethanol (Invitrogen), 0.1 mM non-essential amino acid stock (Invitrogen), and 0.1% huLIF (human leukemia inhibitory factor) conditioned medium. The latter had been produced by transient transfection of a huLIF expression plasmid into human embryonic kidney 293 T cells. Every three to four days colonies were detached with 0.2% collagenase IV (Invitrogen), dissociated into single cells with 0.025% trypsin (Sigma-Aldrich) and 0.1% chicken serum (Invitrogen) in phosphate-buffered saline (PBS) and plated again onto MEFs.

Prior to the initiation of differentiation, pluripotent stem cells were cultured and expanded for several passages on 6-well culture dishes (Thermo Scientific) coated with 0.1% gelatin. The medium (see above) was supplemented with 1 µM inhibitor of glycogen synthase kinase-3 (Merck).

Example 3: In Vitro Lung Epithelial Differentiation of Pluripotent Stem Cells

Before starting the differentiation, pluripotent stem cells were cultivated for several passages without feeder cells to eliminate contaminating MEFs.

Colonies were detached with 0.2% collagenase IV and dissociated into single cells with 0.025% trypsin and 0.1% chicken serum.

Pluripotent stem cells were either differentiated via a 3D embryoid body-based or a 2D monolayer-based differentiation protocol:

1) Embryoid Body-Based Differentiation Protocol

This method is based on our 2008 published differentiation protocol[3]. To initiate embryoid body (EB) formation "hanging drops" composed of $6 \times 10^2$ cells in 20 µl of differentiation medium were generated (day 0 of differentiation). At day 3 of differentiation, EBs (100 EBs/dish) were transferred to non-adherent petri dishes (Greiner) and cultivated in suspension for two additional days. At day 5 of differentiation, 10 EBs/well were seeded on a 0.1% gelatin-coated 6-well culture dish and cultured until day 24 of differentiation. From day 0 to 7 the basal differentiation medium was composed of Iscove's Modified Dulbecco's Medium (IMDM, Invitrogen), 0.2 mM L-glutamine, 0.1 mM β-mercaptoethanol, 0.1 mM non-essential amino acid stock supplemented with 15% FCS and from day 7 to 24 supplemented with 15% serum replacement (Knockout™ SR, Invitrogen). The basal differentiation medium was supplemented with the following growth factors in different combinations and starting at different time points during differentiation: 20 ng/ml recombinant human keratinocyte growth factor (KGF; Amgen Inc., CA, USA) and a three factor combination of 10 nM dexamethasone (Sigma)+0.1 mM 8-bromoadenosine 3′:5′-cyclic monophosphate sodium (Sigma)+0.1 mM 3-isobutyl-1-methylxanthine (Sigma), the combination abbreviated as DCI. The time points of application were the following:

| | | | |
|---|---|---|---|
| KGF: | day 0-24 | KGF (fix) + DCI: | day 0-24 (KGF), day 10-24 (DCI) |
| | day 5-24 | | day 0-24 (KGF), day 14-24 (DCI) |
| | day 17-24 | | day 0-24 (KGF), day 17-24 (DCI) |
| | | | day 0-24 (KGF), day 21-24 (DCI) |
| DCI: | day 10-24 | control: basal medium (BM) without growth factors | |
| | day 14-24 | | |
| | day 17-24 | | |
| | day 21-24 | | |

The differentiation medium was replaced by fresh medium every two to three days. The differentiation was stopped on day 24 and differentiation cultures were analyzed for the presence of lung epithelial cells.

2) Monolayer-Based Differentiation Protocol

For monolayer-based differentiation $6 \times 10^3$ cells were seeded per well on a 0.1% gelatin+5 µg/ml bovine fibronectin (Sigma)-coated 6-well culture dish in culture medium for "undifferentiated cells" (see cultivation of pluripotent stem cells) supplemented with 1 µM inhibitor of glycogen synthase kinase-3. The next day (day 0 of differentiation) the medium was replaced by the following serum-free basal differentiation medium: Advanced RPMI 1640 (Invitrogen) and 0.2 mM L-glutamine. The medium was supplemented with:

day 2-6: 50 ng/ml Activin A (Mitenyi)
day 14-26: KGF+DCI (same concentrations as mentioned in section "Embryoid body-based differentiation protocol")
day 24-26: 1 µg/ml doxycyline (Sigma) for induction of β-galactosidase expression from the transgenic lacZ gene in CCSP-rtTA/tetO-lacZ iPS cells The differentiation medium was replaced by fresh medium every two to three days. The differentiation was stopped on day 26 and differentiation cultures were analyzed for the presence of bronchial/bronchiolar epithelial cells.

Example 4: Methods to Analyze Lung Epithelial Cell Differentiation

1) Quantitative Real-Time RT-PCR (qRT-PCR)

qRT-PCR was used to quantify mRNA expression of typical lung epithelial markers, in particular for bronchial/bronchiolar and alveolar epithelial cells. Marker mRNA expression was normalized to the mRNA expression of the housekeeping-gene β-actin.

2) X-gal and ImaGene Green™ Staining

Either conventional X-gal staining, with a preceding fixation step, or ImaGene Green™ (Molecular probes) staining for living cells was used to detect and visualize bronchial/bronchiolar epithelial cells which express CCSP-driven β-galactosidase from the transgenic lacZ gene.

3) Electron Microscopy (EM)

EM measurements were used to reveal cells with a typical ultrastructure of lung epithelial cells, in particular of bronchial/bronchiolar and alveolar epithelial cells.

REFERENCES

1. Gadue P, Huber T L, Paddison P J, Keller G M. Wnt and TGF-beta signaling are required for the induction of an in vitro model of primitive streak formation using embryonic stem cells. *Proc Natl Acad Sci USA*. 2006; 103: 16806-16811.
2. Wernig M, Meissner A, Foreman R, Brambrink T, Ku M, Hochedlinger K, Bernstein B E, Jaenisch R. In vitro reprogramming of fibroblasts into a pluripotent ES-cell-like state. *Nature*. 2007; 448:318-324.
3. Winkler M E, Mauritz C, Groos S, Kispert A, Menke S, Hoffmann A, Gruh I, Schwanke K, Haverich A, Martin U. Serum-Free Differentiation of Murine Embryonic Stem Cells into Alveolar Type II Epithelial Cells. *Cloning Stem Cells*. 2008; 10:49-64AC.
4. Fehrenbach H, Fehrenbach A, Pan T, Kasper M, Mason R J. Keratinocyte growth factor-induced proliferation of rat airway epithelium is restricted to Clara cells in vivo. *Eur Respir J*. 2002; 20:1185-1197.
5. Sugahara K, Tokumine J, Teruya K, Oshiro T. Alveolar epithelial cells: differentiation and lung injury. *Respirology*. 2006; 11 Suppl:S28-31.
6. Yano T, Mason R J, Pan T, Deterding R R, Nielsen L D, Shannon J M. KGF regulates pulmonary epithelial proliferation and surfactant protein gene expression in adult rat lung. *Am J Physiol Lung Cell Mol Physiol*. 2000; 279:L1146-1158.

7. Berg T, Cassel T N, Schwarze P E, Nord M. Glucocorticoids regulate the CCSP and CYP2B1 promoters via C/EBPbeta and delta in lung cells. *Biochem Biophys Res Commun.* 2002; 293:907-912.
8. Gonzales L W, Guttentag S H, Wade K C, Postle A D, Ballard P L. Differentiation of human pulmonary type II cells in vitro by glucocorticoid plus cAMP. *Am J Physiol Lung Cell Mol Physiol.* 2002; 283:L940-951.
9. Wang J, Edeen K, Manzer R, Chang Y, Wang S. Chen X, Funk C J, Cosgrove G P, Fang X, Mason R J. Differentiated human alveolar epithelial cells and reversibility of their phenotype in vitro. *Am J Respir Cell Mol Biol.* 2007; 36:661-668.

We claim:

1. A method for the production of differentiated alveolar epithelial type 2 cells-comprising:
   (a) providing a cell population consisting of precursor cells of alveolar epithelial type 2 cells, wherein the precursor cells are stem cells selected from the group consisting of embryonic stem cells, adult stem cells, germline-derived stem cells and induced pluripotent stem cells;
   (b) culturing the cell population of (a) in culture medium to generate a cultured cell population; and
   (c) adding keratinocyte growth factor to the cultured cell population;
wherein the cultured cell population is supplemented with a glucocorticoid, a cAMP analogue and a cAMP elevating agent and wherein said supplementation is simultaneously with the addition of keratinocyte growth factor in step (c), thereby differentiating said precursor cells into alveolar epithelial type 2 cells.

2. The method of claim 1, further comprising isolating the alveolar epithelial type 2 cells produced.

3. The method of claim 1, wherein the glucocorticoid is dexamethasone.

4. The method of claim 1, wherein the cAMP analogue is 8-bromo-cAMP or dibutyryl-cAMP.

5. The method of claim 1, wherein the cAMP elevating agent is isobutylmethylxanthine or forskolin.

6. The method of claim 1, wherein the cell population is cultured in suspension.

7. The method of claim 1, wherein the cell population is cultured as adherent cell culture.

8. The method of claim 1, wherein the cell population consisting of precursor cells is selected from a human cell population, a mouse cell population, a monkey cell population and a porcine cell population.

9. The method of claim 1, wherein the culturing of the cells is in serum-free medium.

10. The method of claim 1, wherein the obtained cells are essentially free of pathogens.

11. The method of claim 1, wherein the differentiated alveolar epithelial type 2 cells are characterised by:
   (a) the expression of surfactant protein C (SP-C) and/or surfactant protein B (SP-B) and/or a cuboidal shape in vivo, lamellar bodies and/or micro-villi for alveolar epithelial type 2 cells.

12. A method for the production of differentiated respiratory epithelial cells comprising:
   (a) providing a cell population consisting of precursor cells of differentiated respiratory epithelial cells, wherein the precursor cells of differentiated respiratory epithelial cells are stem cells selected from the group consisting of embryonic stem cells, adult stem cells, germline-derived stem cells and induced pluripotent stem cells; and
   (b) culturing the cell population of (a) in culture medium to generate a cultured cell population, to which keratinocyte growth factor is subsequently added to the cultured cell population;
wherein the cultured cell population is supplemented with a glucocorticoid, a cAMP analogue and a cAMP elevating agent and wherein said supplementation is prior to or subsequently to the addition of keratinocyte growth factor in step (b),
thereby differentiating said precursor cells into differentiated respiratory epithelial cells, wherein the differentiated respiratory epithelial cells are bronchial epithelial cells or alveolar epithelial type 2 cells.

13. The method of claim 12, further comprising isolating the respiratory epithelial cells produced.

14. The method of claim 12, wherein the differentiated respiratory epithelial cells comprise Clara cells.

15. The method of claim 12, wherein the glucocorticoid is dexamethasone.

16. The method of claim 12, wherein the cAMP analogue is 8-bromo-cAMP or dibutyryl-cAMP.

17. The method of claim 12, wherein the cAMP elevating agent is isobutylmethylxanthine or forskolin.

18. The method of claim 12, wherein the cell population is cultured in suspension.

19. The method of claim 12, wherein the cell population is cultured as adherent cell culture.

20. The method of claim 12, wherein the cell population consisting of precursor cells is selected from a human cell population, a mouse cell population, a monkey cell population and a porcine cell population.

21. The method of claim 12, wherein the culturing of the cells is in serum-free medium.

22. The method of claim 12, wherein the obtained cells are essentially free of pathogens.

23. The method of claim 12, wherein the differentiated respiratory epithelial cells are characterised by at least one of:
   (a) the expression of surfactant protein C (SP-C) and/or surfactant protein B (SP-B) and/or a cuboidal shape in vivo, lamellar bodies and/or micro-villi for alveolar epithelial type 2 cells; and
   (b) the expression of clara cell secretory protein (CCSP), surfactant protein B (SP-B) and/or cytochrome P450 enzymes and/or a dome-shape, microvilli and/or smooth endoplasmic reticulum for bronchial epithelial cells, such as for example Clara cells.

* * * * *